United States Patent [19]
Mettler et al.

[11] 4,301,095
[45] Nov. 17, 1981

[54] AIR FRESHENER DISPENSER

[75] Inventors: Leo L. Mettler, Roseville; Arthur L. Johnson, Sacramento, both of Calif.

[73] Assignee: Product Enterprise, Inc., Sacramento, Calif.

[21] Appl. No.: 179,095

[22] Filed: Aug. 18, 1980

[51] Int. Cl.³ .............................................. B01F 3/04
[52] U.S. Cl. ....................................... 261/30; 239/57; 239/60; 261/96; 261/102; 261/DIG. 17; 261/DIG. 65; 422/124
[58] Field of Search ..................... 261/24, 30, 96, 102, 261/DIG. 17, DIG. 65; 422/120, 122-124, 305, 306; 239/6, 41-43, 54, 56, 60

[56] References Cited
U.S. PATENT DOCUMENTS

| | | | |
|---|---|---|---|
| 2,614,820 | 10/1952 | Boydjieff | 422/124 X |
| 2,629,149 | 2/1953 | Yaffe | 422/124 |
| 3,522,935 | 8/1970 | Lewis | 239/60 X |
| 3,902,877 | 9/1975 | Swaim | 422/123 X |
| 3,976,246 | 8/1976 | Havri et al. | 239/60 X |
| 3,993,444 | 11/1976 | Brown | 261/DIG. 17 |
| 4,059,422 | 11/1977 | Steiner | 261/DIG. 17 |
| 4,166,087 | 8/1979 | Cline et al. | 261/DIG. 17 |

*Primary Examiner*—Richard L. Chiesa
*Attorney, Agent, or Firm*—Mark C. Jacobs

[57] ABSTRACT

A superior room air freshener is disclosed having a short distance of travel from point of entry to egress for the delivery of a volatile liquid refresher. The device is battery operated and can be wall mounted or displayed on a table.

10 Claims, 10 Drawing Figures

[4,301,095]

AIR FRESHENER DISPENSER

FIELD OF INVENTION

This invention relates to air freshening, sweetening, neutralizing, perfuming, sterilizing, moth proofing or otherwise treating devices commonly known in the art as devices for deodorizing rooms, i.e. room deodorizers.

BACKGROUND OF THE INVENTION

In the mid 1950's, volatile deodorizing agents were available as vaporizing liquid deodorants under such trademarks as Air Wick ® and Wizard Wick ®. These deodorants were dispensed from bottles, usually glass, which contained an absorbent wick which was mounted on a wire frame and which wick extended vertically down through the bottle, to the bottom thereof. When the bottle cap was removed, the end of the water frame became accessible and would be pulled up as much as desired, into the air to thereby expose a portion of the wick to the surrounding air. The liquid in the container by the wicking action of the wick, was raised to the top and evaporated into the air to thereby destroy offensive odors and to pleasantly scent the air as with the smell of pine trees. The time required to completely dispel an odor such as cigarette smoke in a given enclosed space, depended upon the extent of projection of the wick from the bottle. Usually this was about two inches above the top of the opening and such wicks were about ¾" wide. With such limited exposure, the amount of deodorant dispensed at any given time, was limited and thus, a comparitively long time was required to deodorize a given enclosed space.

One of the major problems of this type of deodorant was the fact that after the job was done, it was necessary for the home owner to remember to close the bottle in order not to waste the liquid through undesired volatilization. In addition, there is always the hazard that children, pets or even adults, could knock the bottle over, thereby spilling the liquid contents. In the 50's, peel-off labels were not readily available, and as such, bottles that were of a fanciful style, after the labels were removed, were not available.

The world then moved to gel formed products which would sublime in the presence of atmospheric air, to thereby release their active ingredients into the room. These products were constantly releasing their active ingredients into the room, in which they were exposed, by evaporation and/or sublimination. However, depending upon the intended application, it may be desirable to have even more distribution of the vaporized product throughout the environment, than is possible by merely exposing the gel at a fixed location. Thus, in bathrooms which are subject to odor concentrations on being used, the scent available from a sublimating gel or stick-like solid, may not be sufficient at any one time, to overcome an offensive bathroom odor.

The next innovation to come to market, were the deodorant sprays. These had the advantage of quick delivery, with very small particle size droplets which could immediately mask or neutralize an offensive odor. However, due to the problem with the flurocarbons, it became necessary to do away with many of the delivery systems used for such volatilizible liquids.

Whereas the deodorizing sprays require an active useage in order to impart an odor removing composition into the environment of a particular room or chamber, no such physical act is necessary with the device of this invention. The instant device to the contrary, can be operated at all times, quietly, without notice, and without any physical effort.

SUMMARY OF THE INVENTION

The system of the present invention operates to propel air which has been induced by fan, past a cartridge comprising a pad having a readily volatilizible fluid impregnated therein. The air moves past and through the cartridge, to volatilize the liquid and to deliver same to the environment, i.e. the room or chamber in which the product is disposed.

The invention is mechanically simple, may be prepared with low cost materials and components. Since the system is battery operated, it is completely portable and may be used indoors or out as be desired, without regard to the availability of electricity. In view of the fact that the battery art has progressed to the point where relatively small batteries are available in the marketplace, the product has been sized to accomodate batteries as small as the standard size C, or D, such that the total structure including the fan contained therein, weighs no more than one pound, and are readily transportable by even a child from room to room.

Accordingly, it is one object of the present invention to provide an inexpensive and portable apparatus for the induction of air past a cartridge or insert, which has been impregnated with a volatile liquid, which liquid can be delivered by the air movement through the device to the surrounding environment.

It is another object of the invention to provide an air deodorizer having a removeable cartridge such that when the contents of the first cartridge has been exhausted as by evaporation, due to air flow there past, a new cartridge may be inserted.

Another object of the invention is to provide an apparatus for conditioning air with a scent pleasing to those within the surroundings of a selected location.

It is a further object of the present invention to provide an apparatus for the introduction of a selected scent or aroma or odor masking composition into a selected region of ambient air.

It is a yet further object of this invention to provide a room deodorizer which is readily transportable, even by a child from one zone of offensive odor to another.

Other objects and advantages of the instant invention will in part be obvious, and will in part appear hereinafter.

The invention accordingly comprises the features of construction, combination of elements and the arrangement of parts, all of which will be exemplified in the following detailed description, taken in conjunction with the accompanying drawings and the appended claims.

DESCRIPTION OF THE PREFERRED EMBODIMENT

The apparatus of this invention is seen to be an odor conditioner or room air refresher. Device 10 includes a base 11 and a cover 12 as is seen in FIG. 1.

Figure 10:
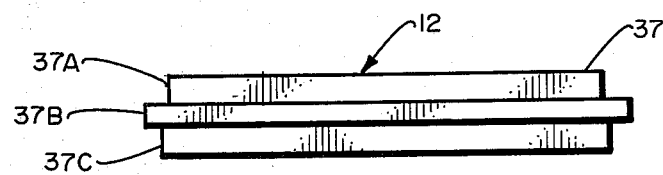
FIG. 10 is an elevational end view of the cover portion of this invention.

The cover has a right section 13, and a left section 17. The right section is a generally planar member having side walls 37 of relatively short elevation. These side walls, per FIG. 10 have a lower portion 37C that frictionally engages the inside of the side panels 27 and the front and rear panels 29 of base 11. For the cover, the same nomenclature is used for both front and back and side walls, but not so far as the base. Side walls 37 further includes an outwarding lip 37B the bottom edge of which rests on the top edge of the front and rear side walls of the base 11. Top portion 37A is sized to be the same cross section of walls 37C as this is part of the company's marketing policy.

Left section of cover 12 includes rectangular upstanding styling 25 which also serves as a guide means to lift the volatile deodorant upward into the room. Extending inwardly at the junction of each pair of said styling bars are four fins 19 set out in an X configuration. Spaced slightly from the junction of said fins and between each pair thereof are vent openings 23 here triangular, though any configuration may be employed. These openings 23 extend through the thickness of the cover and communicate with the interior of the base 11.

Figure 1:
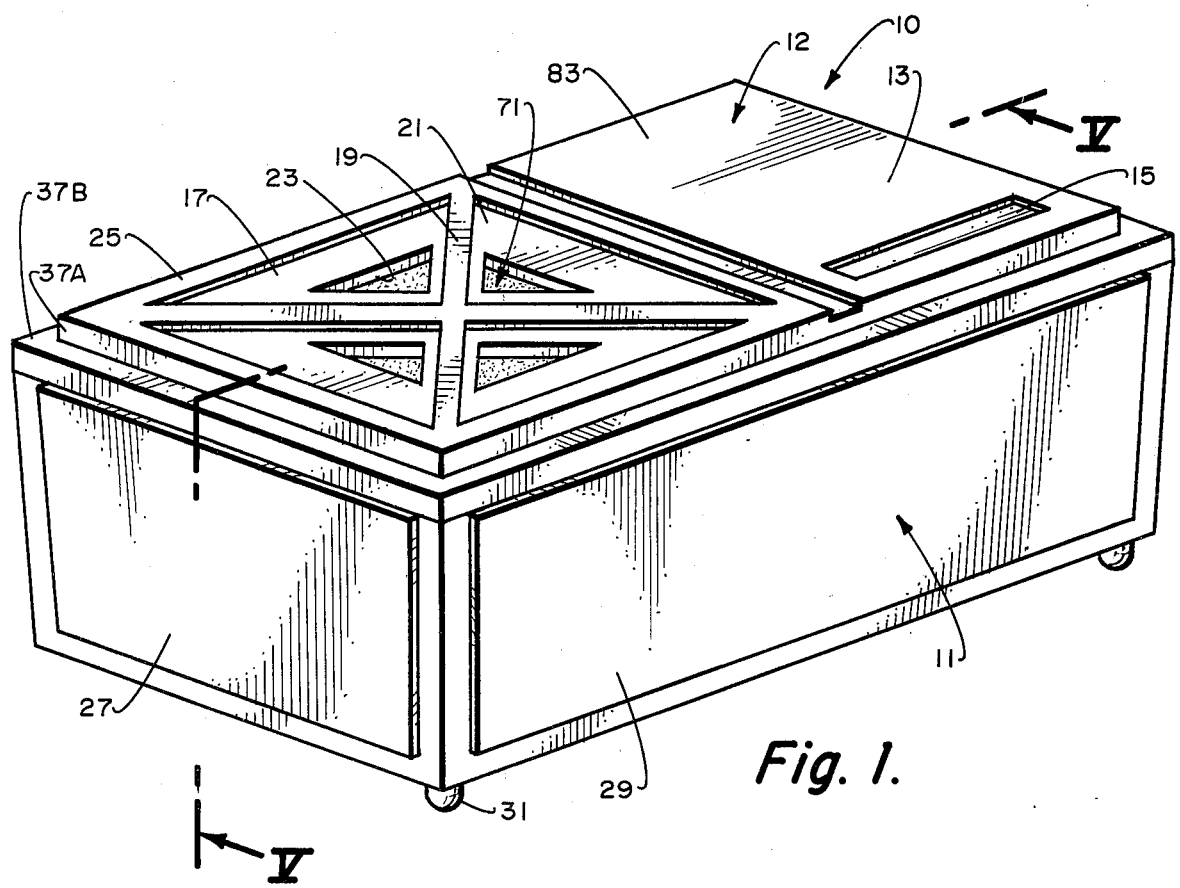
FIG. 1 is a perspective view of the device of this invention.

Also seen in FIG. 1 are the optional depressions 15 in the right section of the cover which serves to receive a label with manufacturing and/or trademark information thereon.

Optional recesses 21 between the fins lend styling to the device. In the same vane, side panels 27 and front and rear panels 29 of base 11 may be entirely flat or include a raised portion as is seen in FIG. 1.

Base 11 includes a floor pan 37 having a plurality of spaced apart feet 31 which may be molded in or attached separately.

In retrospect, it is seen that base 11 is a box having opposed side walls and front and rear walls, all of which are upstanding and all of which extend from the rectangular floor pan 37.

While the base and cover are shown here of a rectangular configuration, obviously other shapes are contemplated as well.

Figure 2:
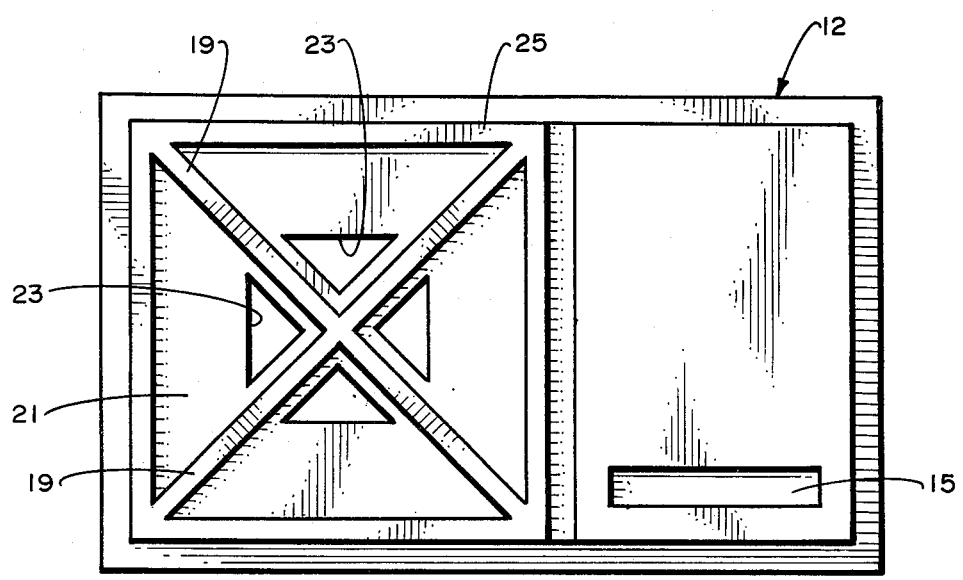
FIG. 2 is a top plan view of the cover.

FIG. 2 is a top plan view illustrating in further detail the fins 19, vents 23, and styling bars 25, all of which have been previously described.

Figure 3:
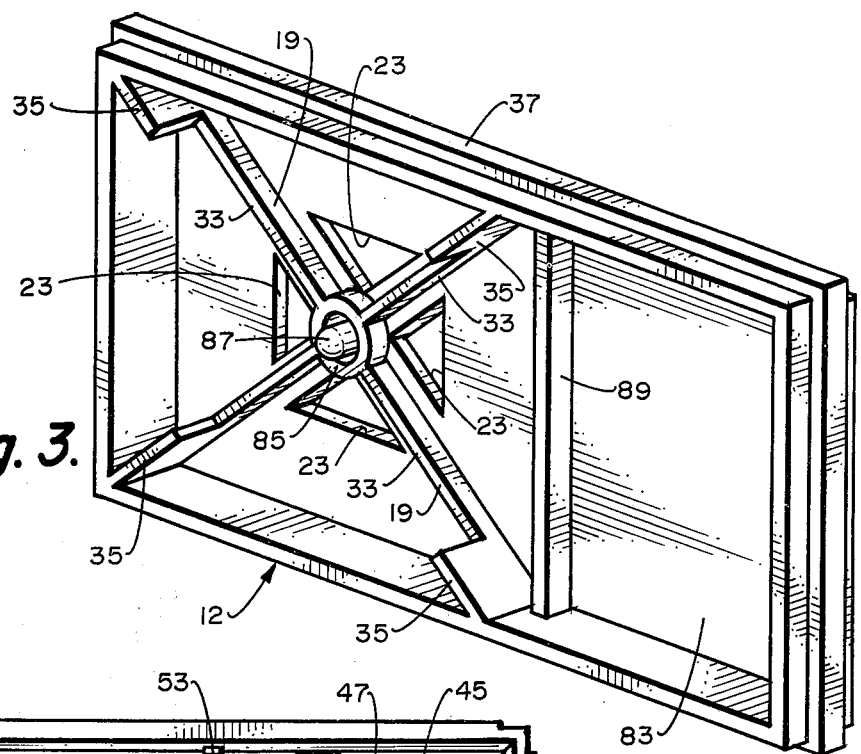
FIG. 3 is a bottom perspective view of the cover.

FIG. 3 is an inside perspective view of cover 12. The cover is seen to be boxlike as well as the configuration of the cross section of the four walls thereof being shown in FIG. 10. Fins 19 are seen to extend beneath the surface of top wall 83, said wall extending into both the left and right sections of cover 12. Fins 19 are seen to be a smaller cross section in the underside of top wall 83 than on the top side. This is optional, and equidimensional underside fins are equally contemplated. The underside of fins 19 are two elevations, a shorter inner part 33 and a taller outer part. On the underside, the fins 19 instead of crossing each other, are normal to an annular member 85 which has a boss 87 disposed therein. The outer higher portions of the fin 35 are sized between opposing pairs to receive wick 71 shown in FIG. 9. Receiver portion 73 frictionally engages boss 87 such that air can flow through and around the wick as will be explained elsewhere herein. Spacer member 89 divides the right section from the left section.

Figure 4:
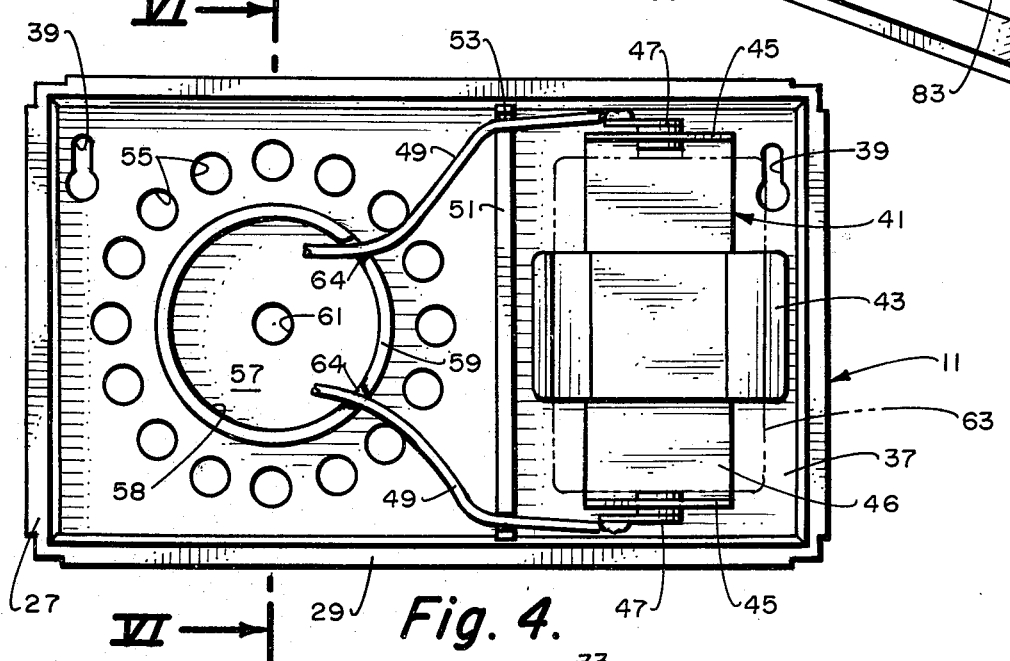
FIG. 4 is a top plan view of the interior of the base portion of this invention with the motor removed.

FIG. 4 is a top plan interior view of base 11. Floor pan 37 is divided into a left and right section by separator 51. Separator 51 is disposed directly beneath spacer 89 when the cover is in place such as to isolate the power section battery from the operative section fan and wick. Separator 51 includes a pair of downwardly extending elongated slots 53, about 1/16th of an inch in diameter which serves to receive and locate wires 49 from the battery to the fan.

Battery holder 41 includes a pair of spaced side walls 43 that extend generally upwardly from bottom pan 46 of said holder 41. These side panels may be curved inwardly as shown in the drawing, FIG. 5, to hold the battery 63 more rigidly in place. End walls 45 extend generally straight up and each of same has a contact terminal 47 mounted thereon, to make electrical contact with the battery. Since holder 41 is of a conventional configuration, further details need not be recited about same other than to indicate that it is adhered or otherwise secured to floor pan 37 to retain same in place.

Figure 5:
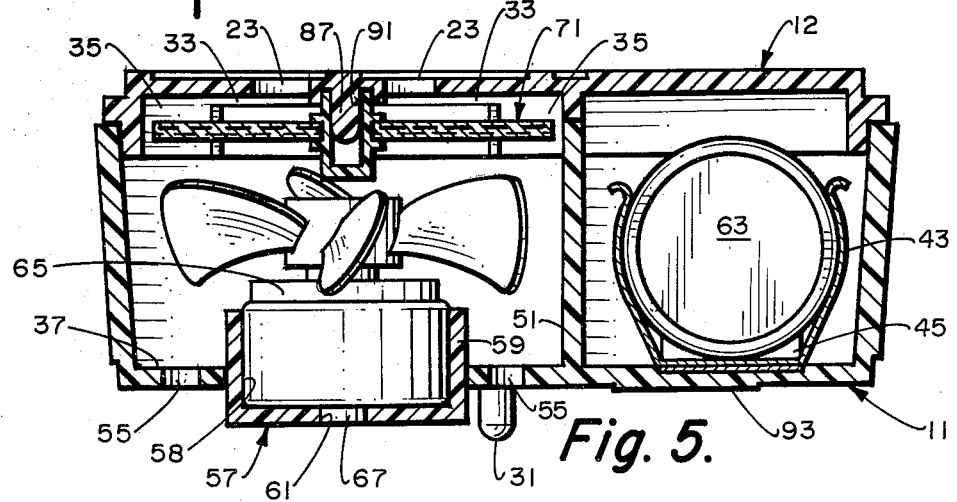
FIG. 5 is a sectional view along the line of V—V of FIG. 1.

Motor mount 57 is secured in opening 58 of floor pan 37 per FIG. 5, or it can be molded in to the base 11 as one part. Motor mount 57 includes a circular side wall 59 adapted to receive a fan motor, now shown. If the motor is square, then motor mount 57 should be configured accordingly. Sidewall 59 as best seen in FIG. 5 depends upward from bottom wall 60. The side wall 59 is seen to extend both above and below the plan of floor pan 37, and bottom wall 60 is disposed parallel to and spaced down from floor pan 37.

Figure 6:
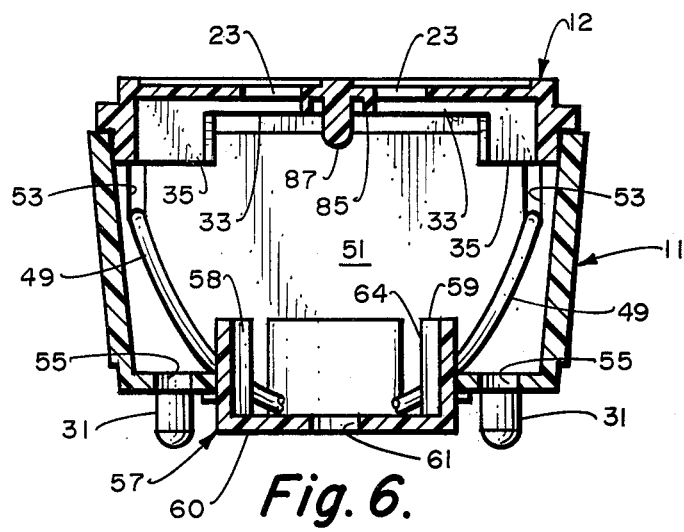
FIG. 6 is a closed section view along the line VI—VI of FIG. 4.

Motor mount 57 is seen to further include a central aperture 61 sized to receive a base 67 on the underside of motor 65 as shown in FIG. 6 by frictional engagement to secure the motor 65 into the central aperture 61.

Side wall 59 also includes a pair of downwardly extending parallel slots 64 adapted to receive lead 49 and to direct said leads to the fan motor 65.

A plurality of openings 55 usually about a 174" diameter, circumscribe motor mount 57 and serve as air intake openings.

One or more optional key hold mount slots 39 may be cut into floor pan 37 to permit this device to be wall mounted if desired.

In reviewing the disclosure just above, it may also be convenient to refer to FIGS. 5 and 6 as well as FIG. 4.

Figure 7:
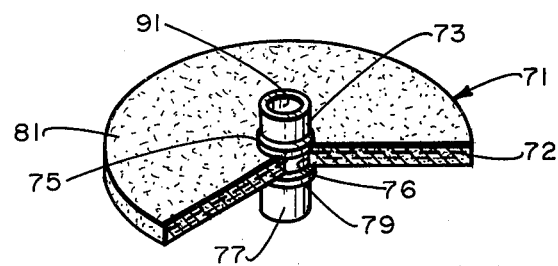
FIG. 7 is a perspective sectional view of a portion of the invention.

FIG. 7 depicts in perspective, the wick 71 which contains the air refreshener which is a volatile liquid 72. Such wick 71 is also designated in the trade as a conditioning element. Said element 71 includes a disc 81 of felt, paper, sponge, or other absorbent material, capable of having volatile fluid 72 delivered therefrom by the impingement of air therein as is seen in exploded view FIG. 9.

Disc 71 has a central aperture 76 through which collar portions 75 and 79 are engaged to retain disc 71 in its operative position on the underside of top wall 83.

Top collar 75 includes an upwardly extending receiving portion 73 adapted to engage boss 87. Bottom collar 79 includes stiffener 77 downwardly disposed therefrom.

Figure 9:
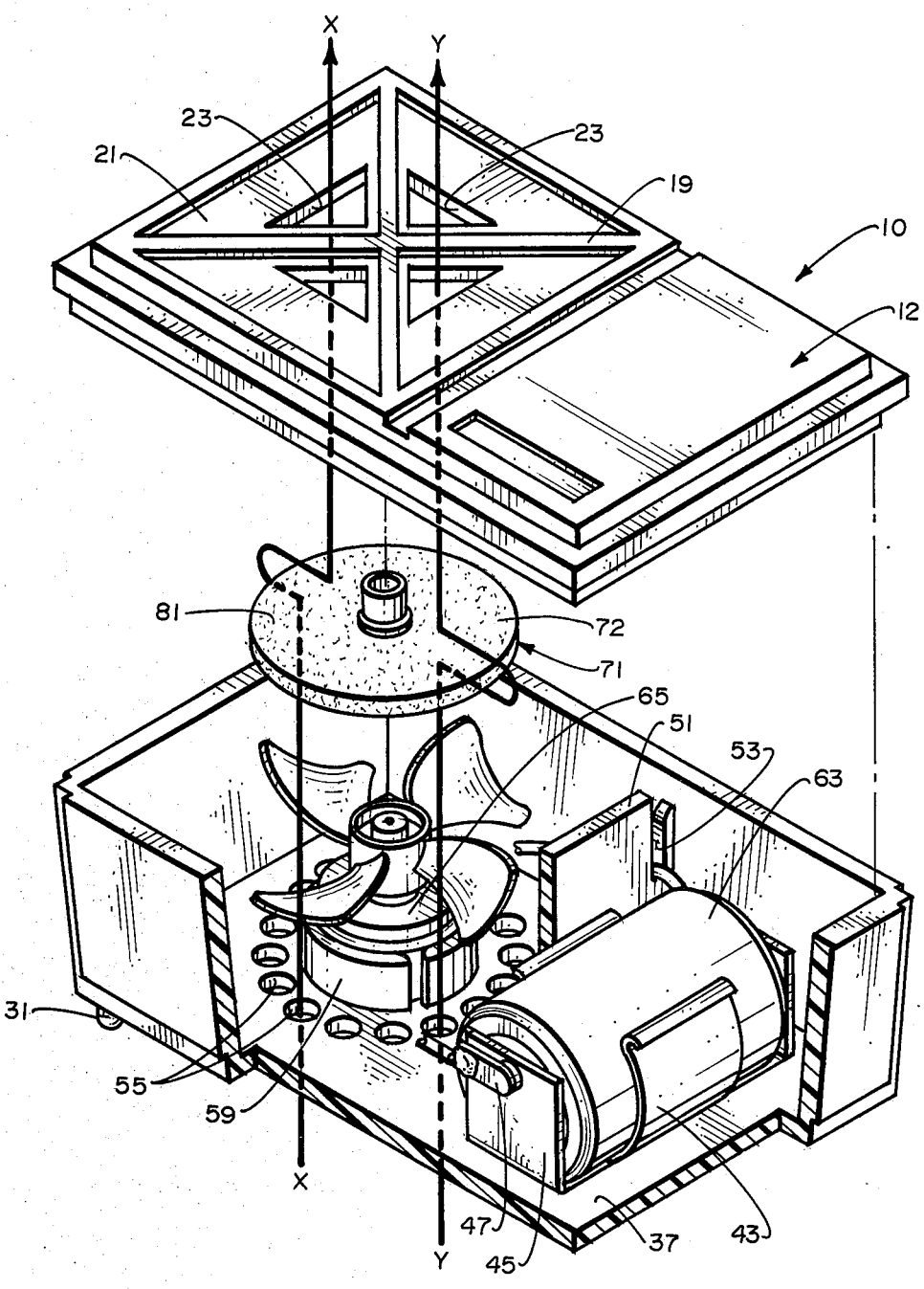
FIG. 9 is an exploded view showing the operation of this device.

Recess 91 which receives boss 87 is sized in depth to maintain disc 81 spaced away from the underside of top wall 83 to permit free flow of air from beneath and around the periphery of the disc 81 such that volatilized fluid can easily escape through triangular openings 23 as is seen in FIG. 9.

Any type of air refreshener 72 known to the art as a volatilizeable fluid may be employed herein.

Figure 8:
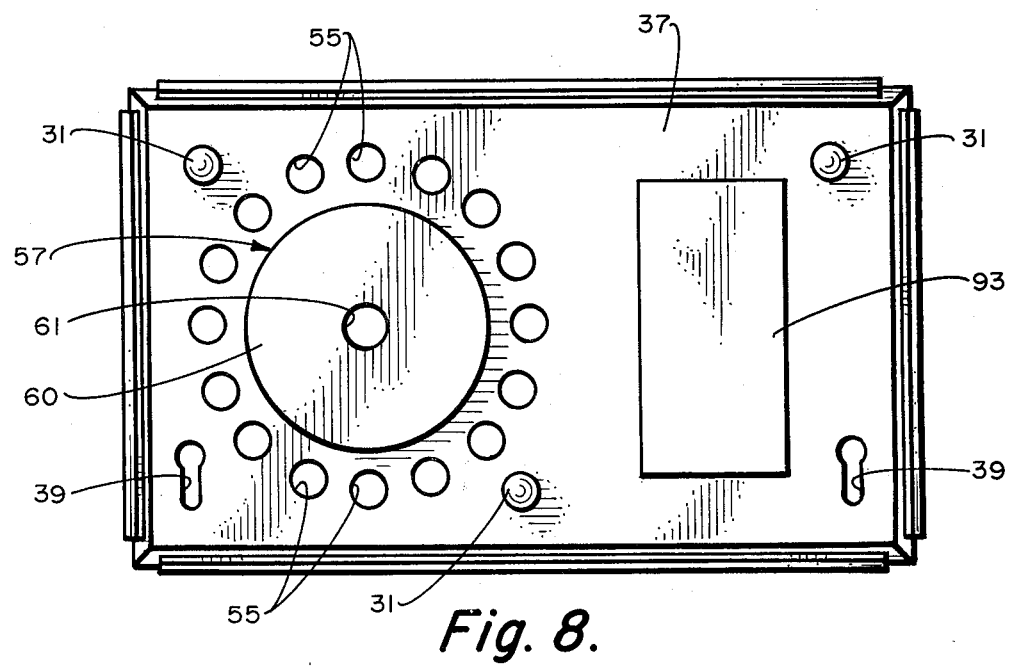
FIG. 8 is a bottom plan view of the device of this invention.

FIG. 8 is a bottom plan view of the device of this invention. Shown herein are motor mount 57 and its central aperture 61. An optional slightly raised label area 93 is shown on the underside of floor pan 37.

It is seen that the key to the ability to deliver a large quantity of volatilized air freshener in a short duration of time, depends upon the coupling of a 360° air intake and a 360° air exhaust as is seen in the exploded diagram, FIG. 9, and described under Operation of the device.

OPERATION

The reader's attention is turned to the exploded view FIG. 9 which shows the air flow pattern of this device that contributes to the superior results obtainable from using same. As is seen in FIG. 9 as well as from FIG. 4, this device employs a 360° air intake flow pattern. That is, air enters through the floor pan 37 in all directions, and impinges upon disc 81. The long lean configuration of device 10 ensures a minimum elevation of travel for air that has impinged upon disc 81 to engage around and through disc 81, and a minimum elevation of travel prior to impingement. Fins 19, specifically underside portion 33 act to direct the air from the motor to element 71 such that substantially all of the air available flows around the conditioning element 71, and across the top of the disc 81 and out the openings 23. Fin portions 19 are sized of an elevation to terminate in a plane corresponding to the underside of disc 81. Thus, they also tend to force air inwardly such that impingement can take place on the top surface of disc 81. While some impingement takes place on the underside of disc 81, the principal contact is seen to be on the top surface of said disc.

In retrospect, it is seen that the flow path is one that is 360° or total circle at the point of air entry. As the air impinges upon the bottom surface of the pad, volatilization takes place. This now volatilized liquid, i.e. in gaseous state, cannot escape downwardly due to pressure from the fan, and since there are no side vents, the flow path continues upwardly around the periphery of the disc.

The fins then direct the air flow across the top of the disc whereby additional refresher is volatilized, and the combined air flow with 2 inputs of refresher material exhaust in a 360° pattern directly above the fan.

This device is the only one known to the inventors which incorporates this dual impingement action.

The importance of the fins cannot be underplayed. If said fins are not present, the air flowing upward does not become divided into four quandrants and is not directed inwardly and thus, over the top of the disc surface. When the fins were omitted for the purpose of testing air flow, it was found that there was reduced impingement on the disc's top surface, and that air swirling was observeable.

While an X shape configuration is shown, any number of radially extending fins that act to break the air volume into a plurality of portions is contemplated. Another suitable number would be six.

It is further seen there is no criticality to shape of device, just so long as the air is permitted to enter and leave in the same direction.

While not shown, an optional on-off switch may be placed in line between the fan and the battery.

As would be anticipated, the fan motor 65 in a low voltage model capable of being powered by a 1.5 volt preferably alkaline battery. The case is easily made from molded plastic such as ABS or styrene, among others, to which can be applied a hot decorative laminate.

When tests were run to compare the air flow movement of this device with the Quiet Breeze unit sold by Amway representatives, it was found that superior results were obtained from this device. The testing procedure comprised passing visible smoke through each device and permitting to exhaust under force from the fan. In the Amway device, the smoke got lost in the interior of the housing, and somewhat later in time, emerged. It got trapped therein due to the large volume of the housing, and the distance of travel between input and output of about 6+ inches. The low profile of the instant device provides a travel distance of only about 2" less from entry to egress. In a preferred version, we were able to reduce travel to about $1\frac{5}{8}$".

As to scents employable herein, any acceptable working agent or scent available in the marketplace may be employed. Depending on the dilution factor, they will last from about 30 to 90 days before expiration. Usually about $\frac{1}{2}$ to 1 ounce is required per disc. The masking agent or scent may be applied as by spraying, dipping or other conventional means to the disc.

Returning momentarily to FIG. 9, air flow lines X and Y serve to illustrate how the air enters through the flow pan 37, passes around and over the top of the disc 81 and then out openings 23, thus yielding superior air flow.

To replace a disc upon exhaustion, one grabs spacer 77 to disengage the frictional fit such that a new element 71 can be installed. After replacement, cover 12 is reinserted into base 11 such that the sidewalls and endwalls frictionally engage, thus restoring the device to an operable condition.

The instant device can be wall mounted or laid to rest on a counter as may be the desire of the user.

We claim:

1. An air freshener unit consisting of a box-like base, a motor carried by said base, an air propeller operatively connected to said motor for propulsion thereby, battery means electrically connected to said motor, feet mounted on the underside of a floor pan of said boxlike base to space the underside thereof away from a contact surface, said floor pan having a series of vertically disposed apertures for the intake of air, said base further including a separator to isolate said battery from said motor, a cover for said base, engageable therewith to control the flow of air through the unit, said cover having a series of radially extending air directing means mounted on the underside thereof, a refresher element removeably secureable to the underside of said cover, said element containing a volatilizeable liquid, said cover including a plurality of openings therein for the egress of air whereby said motor when actuated, air is directed into said unit to impinge upon the underside of the element, around the periphery of said element over the top thereof, and to egress through said openings in said cover.

2. The device of claim 1 further including key hole mount means on the underside of said base.

3. The device of claim 1 wherein the refresher element is a thin disc, frictionally engageable to said cover and adapted to be spaced apart thereof.

4. The device of claim 3 wherein the outer portion of the X shaped fins terminate horizontally just prior to the periphery of the refresher element.

5. The device of claim 1 further including a spacer vertically disposed within the cover, in vertical alignment with the separator to further reduce travel of air from the left, or fan compartment, to the right or battery compartment.

6. The device of claim 1 wherein the motor is a low voltage motor, and the battery is 1½ volts.

7. The device of claim 1 wherein the radially extending air directing means is X-shaped.

8. The device of claim 1 wherein the housing consisting of the floor pan and box-like base is made of plastic.

9. The device of claim 1 wherein the radially extending air directing means on the underside of the cover are in the configuration of X-shaped fins.

10. The device of claim 9 wherein said X shaped fins include a first portion of relatively short elevation, and a terminal second portion whose elevation at its terminal point is in a plane corresponding to the underside of said refresher element.

* * * * *